United States Patent
Takei (10) Patent No.: US 11,096,643 B2
(45) Date of Patent: Aug. 24, 2021

(54) MEDICAL IMAGE PROCESSING APPARATUS, METHOD, AND PROGRAM

(71) Applicant: FUJIFILM Corporation, Tokyo (JP)

(72) Inventor: Mizuki Takei, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 41 days.

(21) Appl. No.: 16/399,203

(22) Filed: Apr. 30, 2019

(65) Prior Publication Data

US 2019/0343473 A1 Nov. 14, 2019

(30) Foreign Application Priority Data

May 9, 2018 (JP) .............................. JP2018-090345

(51) Int. Cl.
*G06K 9/00* (2006.01)
*A61B 6/00* (2006.01)
(Continued)

(52) U.S. Cl.
CPC .............. *A61B 6/501* (2013.01); *A61B 5/055* (2013.01); *A61B 6/032* (2013.01);
(Continued)

(58) Field of Classification Search
CPC . G06T 2207/10081; G06T 2207/30016; G06T 7/0012; G06T 7/11; G06T 7/136; G06T 7/155; G06T 7/0014; G06T 19/00; G06T 2207/10028; G06T 7/60; G06T 17/00; G06T 7/66; G06T 2207/20081; A61B 3/0025; A61B 3/024; A61B 5/4064; A61B 5/7246; A61B 6/5235; A61B 6/5294; A61B 5/107; A61B 5/1171; A61B 5/1176; A61B 2576/026; A61B 5/0205;
(Continued)

(56) References Cited

U.S. PATENT DOCUMENTS

| 6,842,638 B1 * | 1/2005 | Suri ...................... A61B 6/481 382/128 |
| 7,477,768 B2 * | 1/2009 | Kaufman .............. G06T 7/0012 378/41 |

(Continued)

FOREIGN PATENT DOCUMENTS

JP 2011-514822 A 5/2011

OTHER PUBLICATIONS

Atsumi et al., Basal Cistern Effacement and PseudoeSubarachnoid Hemorrhage on Computed Tomography Images of Chronic Subdural Hematoma, 2019, World Neurosurgery 132: e109-e115, Dec. 2019, p. e109-e115.*

(Continued)

*Primary Examiner* — Guillermo M Rivera-Martinez
(74) *Attorney, Agent, or Firm* — Studebaker & Brackett PC (57) ABSTRACT

An image acquisition unit acquires a brain image of a subject. A cisternal region extraction unit extracts a cisternal region from the brain image by performing registration between a standard brain image and the brain image. Then, a bleeding region specifying unit specifies a bleeding region based on a first signal value distribution, which is the signal value distribution of the cisternal region extracted from the brain image, and a second signal value distribution, which is the signal value distribution of a cisternal region of the standard brain image.

12 Claims, 6 Drawing Sheets

(51) Int. Cl.
*A61B 5/055* (2006.01)
*A61B 6/03* (2006.01)
*G06T 7/00* (2017.01)

(52) U.S. Cl.
CPC ....... *A61B 2576/026* (2013.01); *G06T 7/0012* (2013.01); *G06T 2207/10081* (2013.01); *G06T 2207/30016* (2013.01)

(58) Field of Classification Search
CPC .. A61B 5/02241; A61B 5/7267; G16H 50/30; G16H 10/60; G16H 30/20; G16H 30/40; G16H 50/20; G16H 50/50; G16H 50/70; C12Q 2600/158; G01N 2800/52; G01N 15/1475; G06K 9/00281; G06K 9/46; G06K 2209/05; G06K 2209/051; G06F 19/321; G06F 19/325
USPC .......................... 382/128, 129, 130, 131, 132
See application file for complete search history.

(56) References Cited

U.S. PATENT DOCUMENTS

| | | | | |
|---|---|---|---|---|
| 9,492,114 | B2* | 11/2016 | Reiman | A61B 5/0476 |
| 9,901,650 | B2* | 2/2018 | Nedergaard | A61K 49/0032 |
| 2004/0014087 | A1* | 1/2004 | Hodgson | C12Q 1/6876 |
| | | | | 435/6.14 |
| 2006/0039611 | A1* | 2/2006 | Rother | H04N 5/275 |
| | | | | 382/199 |
| 2006/0074290 | A1* | 4/2006 | Chen | G06T 7/97 |
| | | | | 600/407 |
| 2008/0292194 | A1* | 11/2008 | Schmidt | G06T 7/11 |
| | | | | 382/217 |
| 2009/0028403 | A1* | 1/2009 | Bar-Aviv | G16H 50/20 |
| | | | | 382/128 |
| 2009/0196476 | A1* | 8/2009 | Inoue | A61B 1/04 |
| | | | | 382/128 |
| 2009/0202124 | A1* | 8/2009 | Matsuda | G06T 7/0012 |
| | | | | 382/128 |
| 2011/0002523 | A1* | 1/2011 | Prakash | G06T 7/136 |
| | | | | 382/131 |
| 2011/0103657 | A1* | 5/2011 | Kang | A61B 6/504 |
| | | | | 382/128 |
| 2011/0229000 | A1* | 9/2011 | Maroy | G16C 20/30 |
| | | | | 382/131 |
| 2012/0008838 | A1* | 1/2012 | Guyon | G06T 7/66 |
| | | | | 382/128 |
| 2014/0369568 | A1* | 12/2014 | Mangoubi | G06T 7/0012 |
| | | | | 382/108 |
| 2015/0190050 | A1* | 7/2015 | Samadani | A61B 5/7264 |
| | | | | 600/558 |
| 2015/0302584 | A1* | 10/2015 | Brauner | G06T 7/11 |
| | | | | 382/128 |
| 2016/0000945 | A1* | 1/2016 | Nedergaard | A61K 31/41 |
| | | | | 424/1.73 |
| 2016/0038043 | A1* | 2/2016 | Mulligan | G16H 50/50 |
| | | | | 600/301 |
| 2018/0365824 | A1* | 12/2018 | Yuh | G06T 7/0012 |
| 2019/0054022 | A1* | 2/2019 | Macdonald | A61K 9/1652 |

OTHER PUBLICATIONS

Chan et al., 2007, Computer aided detection of small acute intracranial hemorrhage on computer tomography of brain, doi:10.1016/j.compmedimag.2007.02.010, pp. 285-298.*
Celine R. Gillebert et al.; "Automated Delineation of Stroke Lesions Using Brain CT Images"; NeuroImage: Clinical; 2014; pp. 540-548; vol. 4.
An Office Action mailed by the Japan Patent Office dated Jun. 29, 2021, which corresponds to Japanese Patent Application No. 2018-090345 and is related to U.S. Appl. No. 16/399,203; with English translation.
A.M. Boers et al., "Automatic Quantification of Subarachnoid Hemorrhage on Noncontrast CT," AJNR Am J Neuroradiol, Dec. 2014, pp. 2279-2286, vol. 35, No. 12.

* cited by examiner

MEDICAL IMAGE PROCESSING APPARATUS, METHOD, AND PROGRAM

CROSS REFERENCE TO RELATED APPLICATIONS

The present application claims priority under 35 U.S.C. § 119 to Japanese Patent Application No. 2018-090345 filed on May 9, 2018. The above application is hereby expressly incorporated by reference, in its entirety, into the present application.

BACKGROUND

Technical Field

The present invention relates to a medical image processing apparatus, a medical image processing method, and a medical image processing program for extracting a bleeding region suspected of subarachnoid hemorrhage using a brain image, such as a computed tomography (CT) image of the head.

Related Art

In recent years, advances in medical apparatuses, such as CT apparatuses and magnetic resonance imaging (MRI) apparatuses have enabled image diagnosis using high-resolution medical images with higher quality. In particular, in a case where a target part is a brain, a region causing a vascular disorder, such as cerebral infarction and cerebral hemorrhage, can be specified by image diagnosis using CT images, MRI images, and the like. Therefore, appropriate treatment based on the specified result is performed.

Incidentally, for patients suspected of emergency diseases such as subarachnoid hemorrhage, image diagnosis using CT images of the head is often the first choice. For this reason, accurate diagnosis of disease condition using CT images is very important in realizing early treatment. Generally, a bleeding region shows a CT value higher than a surrounding region on a CT image. Therefore, various methods for specifying a bleeding region in the CT image of the head have been proposed. For example, JP2011-514822A has proposed a method of segmenting a reference slice and a CT scan slice, generating a first segmented CT scan slice, and identifying a bleeding slice in CT scan data. In addition, a method of detecting a bleeding region greatly different from a normal region by performing registration between a CT image of a patient and a CT image as a standard model of the brain and comparing CT values in the whole brain has been proposed in Automated delineation of stroke lesions using brain CT images NeuroImage: Clinical, Volume 4, 2014, Pages 540-548.

On the other hand, in subarachnoid hemorrhage, there are cases where the bleeding region shows only a CT value that is almost the same as that of brain parenchyma, unlike in general brain hemorrhage. In this case, in the CT image, the bleeding region and the surrounding region of the bleeding region are displayed with CT values that are almost the same. Even in such a case, a specialist in the brain can specify the bleeding region by looking at the CT image since the specialist in the brain has sufficient anatomical knowledge for the brain. However, patients with subarachnoid hemorrhage are raced to hospitals in many cases. For this reason, doctors who are not specialists in the brain, such as a doctor on duty, perform a first diagnosis in many cases. As described above, in subarachnoid hemorrhage, there are cases where the bleeding region shows only a CT value that is almost the same as that of brain parenchyma. Therefore, in a case where a non-specialist in the brain makes a diagnosis, a bleeding region may be overlooked and accordingly, the start of treatment may be delayed or no treatment may be performed.

According to the methods described in JP2011-514822A and Automated delineation of stroke lesions using brain CT images NeuroImage: Clinical, Volume 4, 2014, Pages 540-548, it is possible to specify a bleeding region in the brain. However, since the entire region of the brain is a target in both the methods, there is a possibility of erroneously detecting a region where subarachnoid hemorrhage cannot occur originally.

SUMMARY

The invention has been made in view of the above circumstances, and it is an object of the invention to make it possible to accurately extract a bleeding region suspected of subarachnoid hemorrhage using a brain image, such as a CT image of the head.

A medical image processing apparatus according to the invention comprises: an image acquisition unit that acquires a brain image of a subject; a cisternal region extraction unit that extracts a cisternal region from the brain image by performing registration between a standard brain image and the brain image; and a bleeding region specifying unit that specifies a bleeding region based on a first signal value distribution, which is a signal value distribution of the cisternal region extracted from the brain image, and a second signal value distribution, which is a signal value distribution of a cisternal region of the standard brain image.

The standard brain image is an image showing an average brain structure, and is created by extracting brain regions from a plurality of medical images, which are acquired by imaging the heads of a plurality of healthy persons with imaging apparatuses, such as CT apparatuses and MRI apparatuses, and averaging the plurality of extracted brain regions. The standard brain image may be created by computer graphics or the like. Alternatively, a brain image of one healthy person may be used as the standard brain image.

In the medical image processing apparatus according to the invention, the bleeding region specifying unit may fit each of the first signal value distribution and the second signal value distribution to a predetermined probability density function, calculate a first probability distribution for the first signal value distribution and a second probability distribution for the second signal value distribution, calculate an index value indicating a difference between the first probability distribution and the second probability distribution, and specify a cisternal region, which is extracted from the brain image for which the calculated index value exceeds a predetermined threshold value, as the bleeding region.

In the medical image processing apparatus according to the invention, the bleeding region specifying unit may comprise a discriminator to which a feature amount based on the first signal value distribution and the second signal value distribution is input and which outputs a determination result as to whether or not the cisternal region is the bleeding region.

In the medical image processing apparatus according to the invention, a probability value indicating a likelihood of being the cisternal region may be set for each pixel of the standard brain image, and the bleeding region specifying unit may calculate the first signal value distribution by weighting a pixel value of each pixel of the brain image registered with the standard brain image further based on the probability value.

In the medical image processing apparatus according to the invention, the cisternal region extraction unit may further divide the cisternal region into a plurality of anatomical regions, and the bleeding region specifying unit may specify the bleeding region based on a first signal value distribution of each of the plurality of anatomical regions and a second signal value distribution of a region, which corresponds to each of the plurality of anatomical regions, in the standard brain image.

In the medical image processing apparatus according to the invention, the bleeding region specifying unit may specify the bleeding region using a different parameter in each of the plurality of anatomical regions.

In the medical image processing apparatus according to the invention, the bleeding region specifying unit may comprise a discriminator to which a feature amount based on the first signal value distribution and the second signal value distribution for each of the plurality of anatomical regions is input and which outputs a determination result as to whether or not the cisternal region is the bleeding region.

In the medical image processing apparatus according to the invention, a probability value indicating a likelihood of being the cisternal region may be set for each pixel of the standard brain image, and the bleeding region specifying unit may calculate the first signal value distribution for each of the plurality of anatomical regions by weighting a pixel value of each pixel of the brain image registered with the standard brain image further based on the probability value.

In the medical image processing apparatus according to the invention, the brain image may be a CT image acquired by a CT apparatus.

The medical image processing apparatus according to the invention may further comprise a display control unit that displays information indicating that the bleeding region has been specified on a display unit.

A medical image processing method according to the invention comprises: acquiring a brain image of a subject; extracting a cisternal region from the brain image by performing registration between a standard brain image and the brain image; and specifying a bleeding region based on a first signal value distribution, which is a signal value distribution of the cisternal region extracted from the brain image, and a second signal value distribution, which is a signal value distribution of a cisternal region of the standard brain image.

In addition, a program causing a computer to execute the medical image processing method according to the invention may be provided.

Another medical image processing apparatus according to the invention comprises: a memory that stores commands to be executed by a computer; and a processor configured to execute the stored commands. The processor executes processing of: acquiring a brain image of a subject; extracting a cisternal region from the brain image by performing registration between a standard brain image and the brain image; and specifying a bleeding region based on a first signal value distribution, which is a signal value distribution of the cisternal region extracted from the brain image, and a second signal value distribution, which is a signal value distribution of a cisternal region of the standard brain image.

In subarachnoid hemorrhage, bleeding occurs in the cisternae in the brain. In the brain image of a normal brain, since a cisternal region is filled with cerebrospinal fluid, the cisternal region shows a unique value (for example, a low CT value in the case of a CT image) corresponding to the type of the medical image. Therefore, the cisternal region is displayed with a CT value different from that of a region of brain parenchyma therearound. For this reason, by specifying the position of a cisternal region in a medical image of the brain, that is, a brain image, it is possible to extract a region suspected of subarachnoid hemorrhage with high accuracy.

According to the invention, a cisternal region is extracted from the brain image of the brain of the subject by performing registration between the standard brain image and the brain image, and a bleeding region is specified based on the first signal value distribution, which is the signal value distribution of the cisternal region extracted from the brain image, and the second signal value distribution, which is the signal value distribution of the cisternal region of the standard brain image. For this reason, in the brain image, it is possible to check the presence or absence of bleeding after accurately specifying a region suspected of bleeding due to subarachnoid hemorrhage. Therefore, it is possible to accurately diagnose subarachnoid hemorrhage using the brain image of the head.

DETAILED DESCRIPTION

Figure 1:
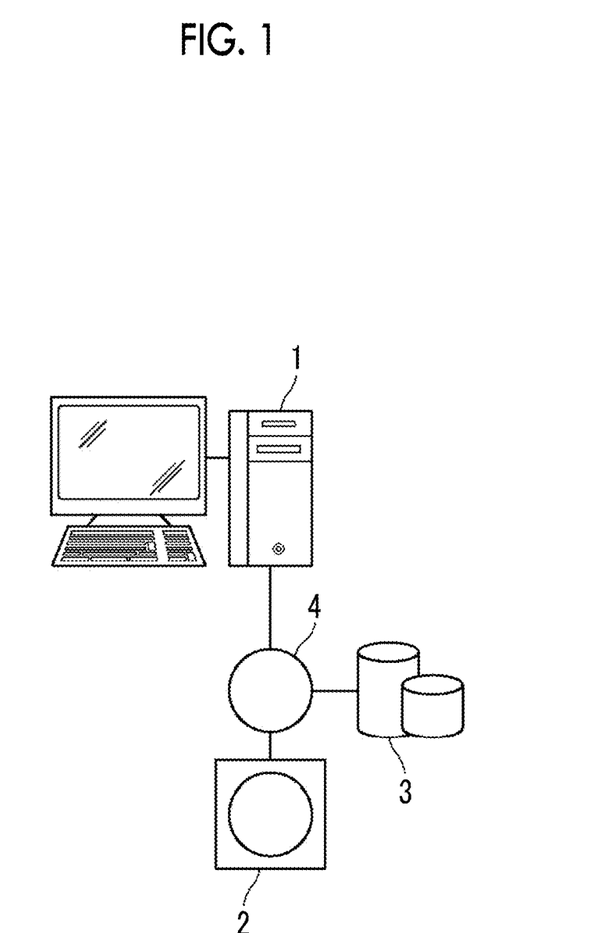
FIG. 1 is a hardware configuration diagram showing the outline of a diagnostic support system to which a medical image processing apparatus according to an embodiment of the invention is applied.

Hereinafter, embodiments of the invention will be described with reference to the diagrams. FIG. 1 is a hardware configuration diagram showing the outline of a diagnostic support system to which a medical image processing apparatus according to a first embodiment of the invention is applied. As shown in FIG. 1, in the diagnostic support system, a medical image processing apparatus 1 according to the present embodiment, a three-dimensional image capturing apparatus 2, and an image storage server 3 are communicably connected to each other through a network 4.

The three-dimensional image capturing apparatus 2 is an apparatus that generates a three-dimensional image showing a part, which is an examination target part of a subject, as a medical image by imaging the part. Specifically, the three-dimensional image capturing apparatus 2 is a CT apparatus, an MRI apparatus, a positron emission tomography (PET)

apparatus, or the like. The medical image generated by the three-dimensional image capturing apparatus 2 is transmitted to the image storage server 3 and is stored therein. In the present embodiment, the diagnostic target part of a patient as a subject is the brain, and the three-dimensional image capturing apparatus 2 is a CT apparatus and generates a CT image of the head containing the brain of the subject as a three-dimensional brain image B0.

The image storage server 3 is a computer that stores and manages various kinds of data, and includes a large-capacity external storage device and software for database management. The image storage server 3 performs communication with other apparatuses through the wired or wireless network 4 to transmit and receive image data or the like. Specifically, the image storage server 3 acquires various kinds of data including the image data of the brain image B0 generated by the three-dimensional image capturing apparatus 2 through the network, and stores the various kinds of data in a recording medium, such as a large-capacity external storage device, and manages the various kinds of data. The storage format of image data and the communication between apparatuses through the network 4 are based on a protocol, such as a digital imaging and communication in medicine (DICOM).

The medical image processing apparatus 1 is realized by installing a medical image processing program of the invention on one computer. The computer may be a workstation or a personal computer that is directly operated by a doctor who performs diagnosis, or may be a server computer connected to these through a network. The medical image processing program is recorded on a recording medium, such as a digital versatile disc (DVD) or a compact disc read only memory (CD-ROM), so as to be distributed, and is installed onto the computer from the recording medium. Alternatively, the medical image processing program is stored in a storage device of a server computer connected to the network or in a network storage so as to be accessible from the outside, and is downloaded and installed onto a computer used by a doctor as necessary.

Figure 2:
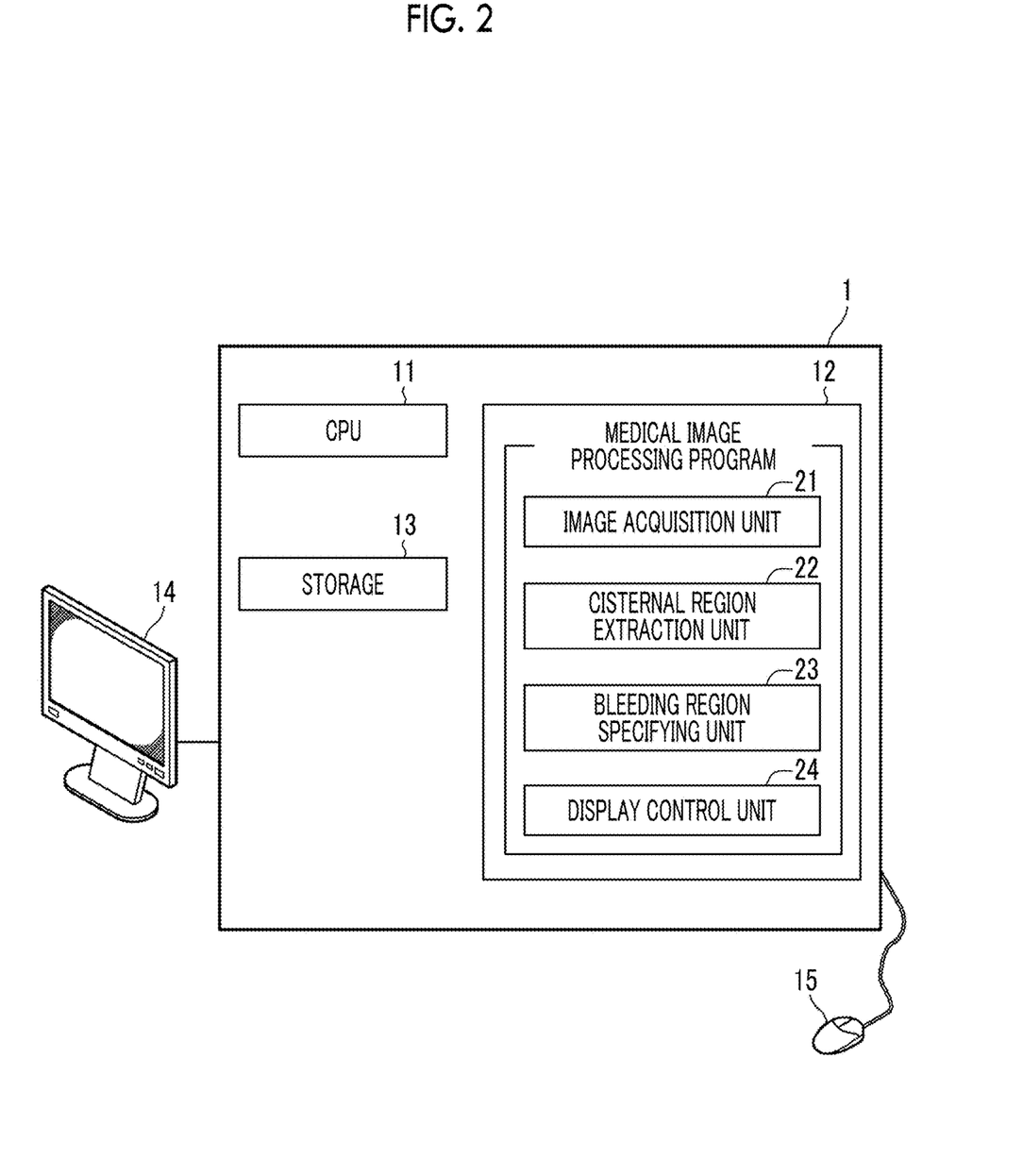
FIG. 2 is a diagram showing the schematic configuration of a medical image processing apparatus according to a first embodiment.

FIG. 2 is a diagram showing the schematic configuration of a medical image processing apparatus realized by installing a medical image processing program on a computer. As shown in FIG. 2, the medical image processing apparatus 1 includes a central processing unit (CPU) 11, a memory 12, and a storage 13 as the configuration of a standard workstation. A display 14 and an input unit 15, such as a keyboard and a mouse, are connected to the medical image processing apparatus 1. The display 14 corresponds to a display unit.

Brain images of the subject and various kinds of information including information required for processing, which are acquired from the image storage server 3 through the network 4, are stored in the storage 13.

A medical image processing program is stored in the memory 12. As processing to be executed by the CPU 11, the medical image processing program defines image acquisition processing for acquiring the brain image B0 of a subject, cisternal region extraction processing for extracting a cisternal region from the brain image B0 by performing registration between a standard brain image and the brain image B0, bleeding region specifying processing for specifying a bleeding region based on the first signal value distribution that is the signal value distribution of the cisternal region extracted from the brain image B0 and the second signal value distribution that is the signal value distribution of the cisternal region of the standard brain image, and display control processing for displaying information indicating that the bleeding region has been specified on the display 14.

Then, the CPU 11 executes these processes according to the program, so that the computer functions as an image acquisition unit 21, a cisternal region extraction unit 22, a bleeding region specifying unit 23, and a display control unit 24. In the present embodiment, the CPU 11 executes the function of each unit according to the medical image processing program. However, as a general-purpose processor that executes software to function as various processing units, a programmable logic device (PLD) that is a processor whose circuit configuration can be changed after manufacturing, such as a field programmable gate array (FPGA), can be used in addition to the CPU 11. Alternatively, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). Alternatively, a plurality of processing units may be configured by one processor. As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

The image acquisition unit 21 acquires the brain image B0 of the brain of the subject from the image storage server 3. In a case where the brain image B0 is already stored in the storage 13, the image acquisition unit 21 may acquire the brain image B0 from the storage 13.

Figure 3:
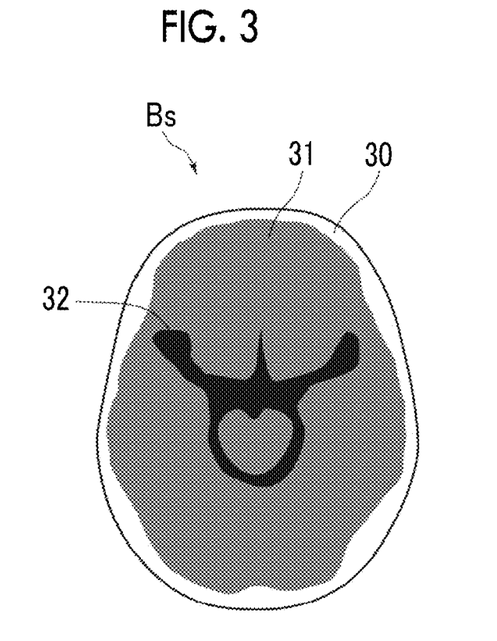
FIG. 3 is a drawing showing a standard brain image.

The cisternal region extraction unit 22 extracts a cisternal region from the brain image B0 by performing registration between a standard brain image and the brain image B0. The standard brain image is a brain image generated by extracting brain regions from a plurality of CT images, which are acquired by imaging the heads of a plurality of healthy persons with a CT apparatus, to generate a plurality of brain images and averaging the plurality of brain images. In the present embodiment, the brain region includes brain parenchyma and skull. However, the brain region may include only brain parenchyma. FIG. 3 is a diagram showing a standard brain image. Although the standard brain image is a three-dimensional image showing the brain, a tomographic image of the brain in a certain cross section is shown in FIG. 3 for the purpose of description. As shown in FIG. 3, a standard brain image Bs includes a skull 30 and brain parenchyma 31, and the brain parenchyma 31 includes a cisternal region 32. Actually, the brain parenchyma 31 includes other anatomical regions such as a cerebral ventricle. However, only the cisternal region 32 is shown in FIG. 3. Image data of the standard brain image Bs is stored in the image storage server 3 or the storage 13, and the cisternal region extraction unit 22 acquires the image data of the standard brain image Bs from the image storage server 3 or the storage 13.

The standard brain image Bs may be created by computer graphics or the like. Alternatively, a brain image of one healthy person may be used as the standard brain image Bs.

As shown in FIG. 3, in the standard brain image Bs, the skull 30 is shown in white since the skull 30 has a very high CT value and the brain parenchyma 31 is shown in gray. In addition, the cisternal region 32 has a very low CT value since the cisternal region 32 is filled with cerebrospinal fluid. Accordingly, the cisternal region 32 is shown in black.

Figure 4:
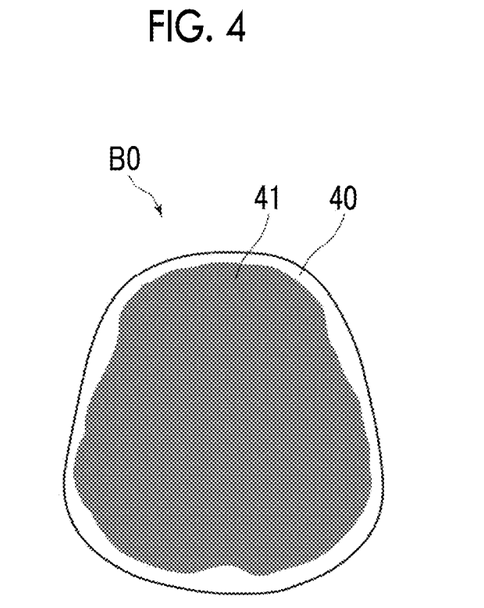
FIG. 4 is a diagram showing a brain image of a subject.

Here, the shape and size of the head differ depending on the subject. For example, as shown in FIG. 4, the shape and size of the brain included in the brain image B0 of the subject are different from the shape and size of the brain included in the standard brain image Bs shown in FIG. 3. In FIG. 4, only a skull 40 and brain parenchyma 41 are shown, and cisternae are omitted.

The cisternal region extraction unit 22 performs registration between the brain image B0 and the standard brain image Bs in order to extract a region of a cisterna (hereinafter, referred to as a cisternal region) from the brain image B0. The registration is performed between the three-dimensional brain image B0 and the three-dimensional standard brain image Bs. As a method of registration, first registration between the standard brain image Bs and the brain image B0 is performed first using landmarks. Then, after performing the first registration, second registration between the standard brain image Bs and the brain image B0 is performed using the entire region. As a landmark, specifically, at least one of characteristic regions, such as a cerebral groove and a cerebral ventricle contained in the brain, can be used.

The cisternal region extraction unit 22 performs the first registration between the standard brain image Bs and the brain image B0 so that the corresponding landmarks match each other. In the present embodiment, the first registration is registration by similarity transformation. Specifically, the first registration is registration by parallel movement, rotation, and similar enlargement and reduction of the brain image B0. The cisternal region extraction unit 22 performs the first registration by performing similarity transformation of the brain image B0 so that the correlation between a landmark included in the standard brain image Bs and a landmark, which is included in the brain image B0 and corresponds to the landmark of the standard brain image Bs, is maximized.

After performing the first registration using the landmarks as described above, the cisternal region extraction unit 22 performs the second registration using the entire region between the standard brain image Bs and the brain image B0. In the present embodiment, the second registration is registration by nonlinear transformation. As the registration by nonlinear transformation, for example, there is registration performed by nonlinearly converting pixel positions using functions, such as B spline and thin plate spline. The cisternal region extraction unit 22 performs the second registration by nonlinearly converting each pixel position of the brain image B0 after the first registration to a corresponding pixel position included in the standard brain image Bs.

Figure 5:
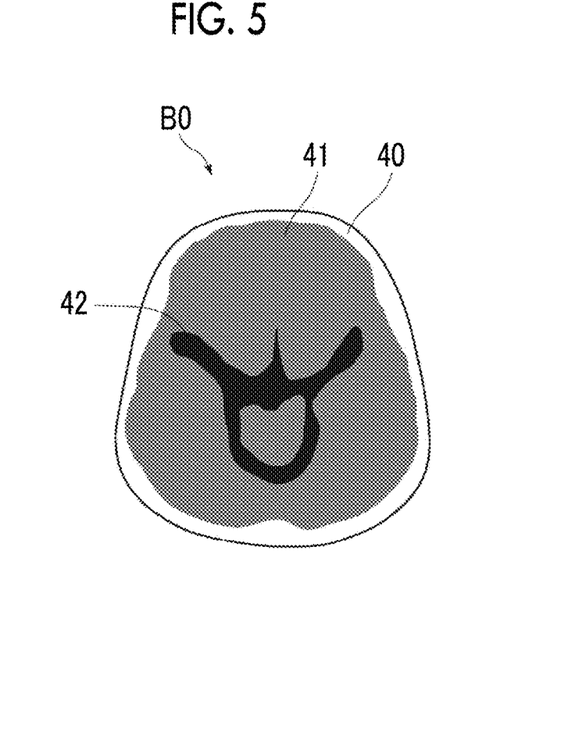
FIG. 5 is a diagram showing a cisternal region extracted from a brain image.

By performing the registration as described above, it is possible to associate a cisternal region in the brain image B0 with a cisternal region in the standard brain image Bs. Then, the cisternal region extraction unit 22 extracts a region in the brain image B0, which is associated with the cisternal region of the standard brain image Bs, as a cisternal region 42 of the brain image B0. FIG. 5 is a diagram showing a cisternal region extracted from the brain image B0. As shown in FIG. 5, in the brain image B0, the cisternal region 42 is extracted. In addition, in FIG. 5, the cisternal region 42 is shown in black.

The bleeding region specifying unit 23 specifies a bleeding region. Specifically, the bleeding region specifying unit 23 specifies a bleeding region based on the first signal value distribution, which is the signal value distribution of the cisternal region 42 extracted from the brain image B0, and the second signal value distribution, which is the signal value distribution of the cisternal region (hereinafter, 32 is also used as a reference number for the cisternal region 32) 32 of the standard brain image Bs. Generally, a bleeding region shows a high CT value on the CT image. However, in subarachnoid hemorrhage, there are cases where the bleeding region shows only a CT value that is almost the same as that of brain parenchyma, unlike in general brain hemorrhage. On the other hand, in subarachnoid hemorrhage, bleeding is observed in a cisternal region.

The bleeding region specifying unit 23 compares the distributions of pixel values (CT values), that is, signal value distributions of the cisternal region 42 extracted from the brain image B0 and the cisternal region 32 in the standard brain image Bs corresponding to the cisternal region 42. Therefore, the bleeding region specifying unit 23 fits the distribution of each pixel value (CT value) in the cisternal region 42 of the brain image B0, that is, the first signal value distribution that is a signal value distribution, and the second signal value distribution, which is the signal value distribution in the cisternal region 32 of the standard brain image Bs, to the probability density function of normal distribution. A histogram of pixel values in the cisternal region 42 is used for the first signal value distribution, and a histogram of pixel values in the cisternal region 32 is used for the second signal value distribution.

Here, in a case where the CT values of all the pixels in the cisternal regions 32 and 42 are collected as samples, the average value and the variance value of the pixel values in the cisternal regions 32 and 42 can be calculated. Once the average value and the variance value are calculated, the probability density function of normal distribution can be uniquely defined. Therefore, the bleeding region specifying unit 23 calculates a probability density function (hereinafter, referred to as a first probability density function) for the cisternal region 42 based on the pixel values in the cisternal region 42 extracted from the brain image B0. In addition, the bleeding region specifying unit 23 calculates a probability density function (hereinafter, referred to as a second probability density function) for the cisternal region 32 based on the pixel values in the cisternal region 32 extracted from the standard brain image Bs.

Therefore, the bleeding region specifying unit 23 fits the first signal value distribution to the first probability density function, and fits the second signal value distribution to the second probability density function. In addition, the bleeding region specifying unit 23 calculates an index value indicating the difference in normal distribution between the fitted first signal value distribution and the fitted second signal value distribution. For example, Kullback-Leibler (KL)-divergence can be used as an index value indicating the difference. Then, in a case where the calculated index value exceeds a predetermined threshold value Th1, the cisternal region 42 of the brain image B0 is specified as a bleeding region.

Figure 6:
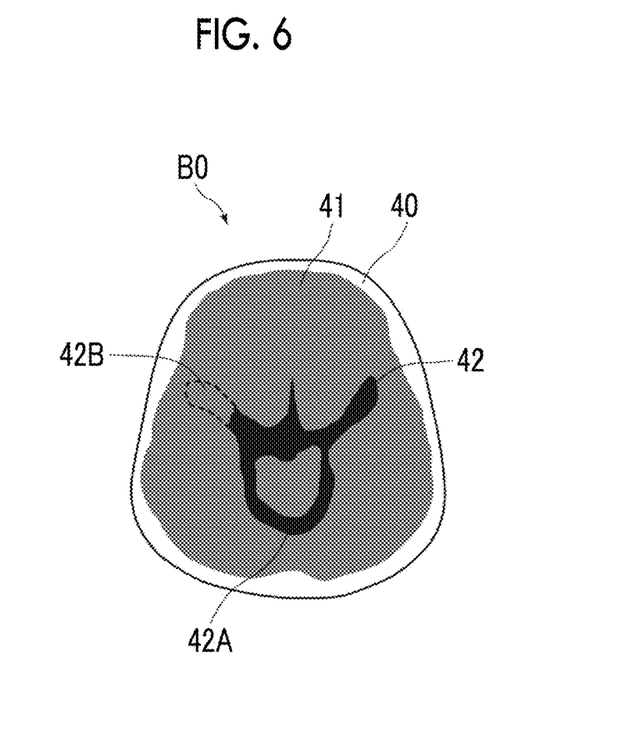
FIG. 6 is a diagram illustrating the specification of a bleeding region.

FIG. 6 is a diagram illustrating the specification of a bleeding region. As shown in FIG. 6, the cisternal region 42 of the brain image B0 includes a region 42A having a relatively low CT value and a region 42B having almost the same CT value as the brain parenchyma 41. In this case, the region 42B has almost the same CT value as the brain parenchyma 41 since there is bleeding. For this reason, the index value calculated as described above exceeds the threshold value Th1. Therefore, the bleeding region specifying unit 23 specifies the cisternal region 42 as a bleeding region.

Figure 7:
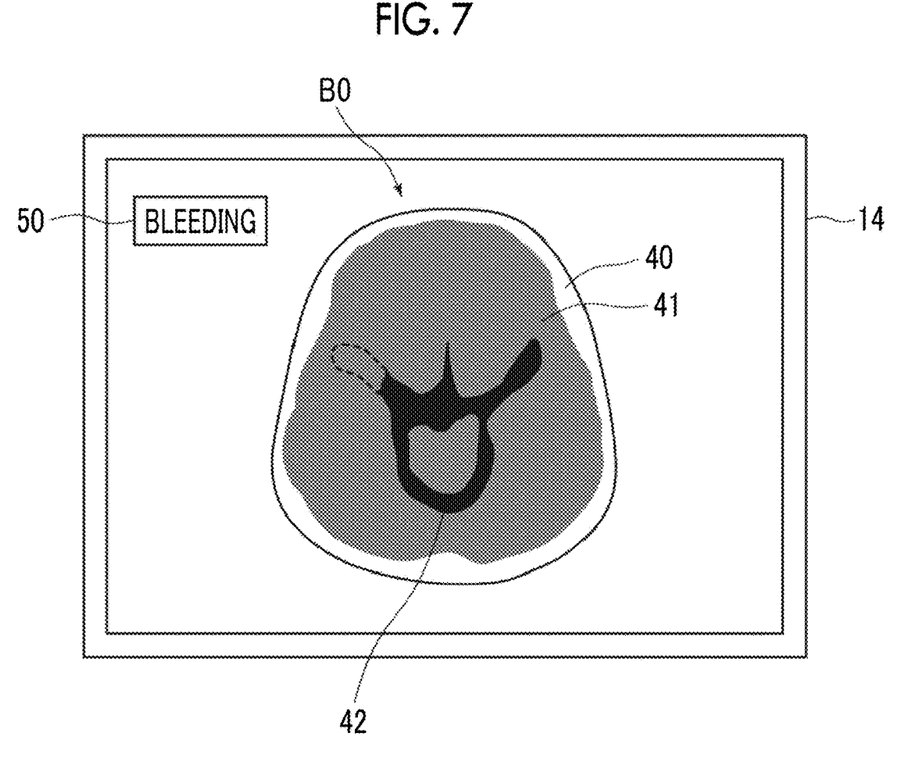
FIG. 7 is a diagram showing a brain image displayed on a display.

The display control unit 24 displays information indicating that the bleeding region has been specified on the display 14. FIG. 7 is a diagram showing the brain image B0 displayed on the display. As shown in FIG. 7, on the display 14, a text 50 indicating that the cisternal region 42 is a bleeding region is displayed as the information indicating that the bleeding region has been specified. By displaying the text 50 indicating that the cisternal region 42 is a bleeding region on the display 14 as described above, the doctor can carefully observe the cisternal region 42 in the brain image B0 of the subject. Therefore, the doctor can easily recognize a bleeding region.

The information indicating that the bleeding region has been specified is not limited to the text 50 but may be information other than texts, such as symbols and icons.

Figure 8:
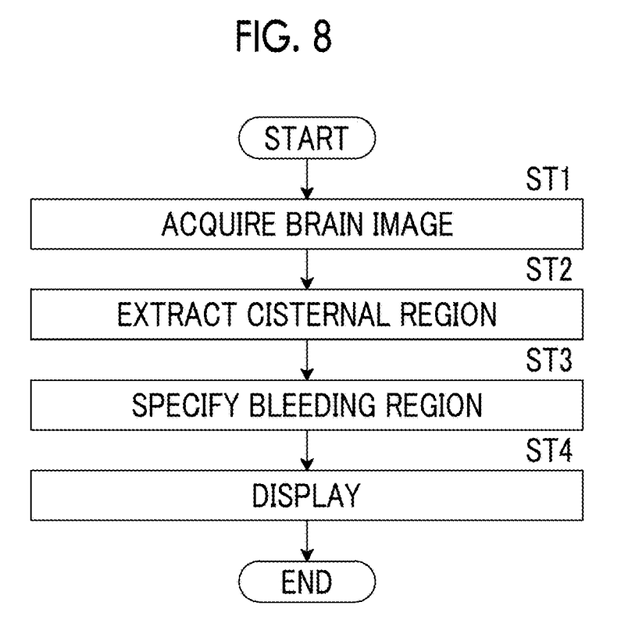
FIG. 8 is a flowchart showing the process performed in the present embodiment.

Next, the process performed in the first embodiment will be described. FIG. 8 is a flowchart showing the process performed in the first embodiment. First, the image acquisition unit 21 acquires the brain image B0 of a subject (step ST1). Then, the cisternal region extraction unit 22 extracts a cisternal region from the brain image B0 by performing registration between the standard brain image Bs and the brain image B0 (step ST2). Then, the bleeding region specifying unit 23 specifies a bleeding region based on the first signal value distribution, which is the signal value distribution of the cisternal region extracted from the brain image B0, and the second signal value distribution, which is the signal value distribution of the cisternal region of the standard brain image (step ST3). Then, the display control unit 24 displays information indicating that the bleeding region has been specified on the display 14 (step ST4), and ends the processing.

As described above, in the first embodiment, the cisternal region 42 is extracted by performing registration between the standard brain image Bs and the brain image B0, and a bleeding region is specified based on the first signal value distribution, which is the signal value distribution of the cisternal region 42 extracted from the brain image B0, and the second signal value distribution, which is the signal value distribution of the cisternal region 32 of the standard brain image Bs. For this reason, in the brain image B0, it is possible to check the presence or absence of bleeding after accurately specifying a region suspected of bleeding due to subarachnoid hemorrhage. Therefore, it is possible to accurately diagnose subarachnoid hemorrhage using a brain image.

In the first embodiment described above, a probability value indicating the likelihood of being a cisternal region may be set for each pixel of the standard brain image Bs. The probability value is calculated as follows. That is, registration between a plurality of brain images, from which the standard brain image Bs has been generated, and the standard brain image Bs is performed. Then, for each pixel in the cisternal region 32 of the standard brain image Bs, the percentage of brain images including a cisternal region among the plurality of brain images is calculated as the probability value. Specifically, for each pixel in the cisternal region 32 of the standard brain image Bs, the number of brain images including a cisternal region among the plurality of brain images is counted, and a value obtained by dividing the counted number by the total number of brain images may be used as the probability value.

In this case, based on the probability value, the bleeding region specifying unit 23 weights the pixel value of each pixel of the brain image B0 registered with the standard brain image Bs to calculate the first signal value distribution. Specifically, the CT value of each pixel in the cisternal region 42 is multiplied by the probability value calculated for each pixel in the cisternal region 32 corresponding to each pixel in the cisternal region 42. Then, the first signal value distribution is calculated from the CT value multiplied by the probability value, and a bleeding region is specified using the calculated first signal value distribution. By specifying a bleeding region in this manner, it is possible to specify a bleeding region in a region, which is more likely to be a cisterna, in the brain image B0. Therefore, diagnosis of subarachnoid hemorrhage can be performed more appropriately.

Incidentally, the cisterna can be divided into a plurality of anatomical regions, such as a longitudinal cerebral fissure, a sylvian fissure, a sylvian valley, a basal cistern, and an ambient cistern. Therefore, the cisternal region extraction unit 22 may divide the extracted cisternal region 42 into a plurality of anatomical regions. Hereinafter, an embodiment in which the cisternal region 42 is divided into a plurality of anatomical regions will be described as a second embodiment. Since the configuration of a medical image processing apparatus according to the second embodiment of the invention is the same as the configuration of the medical image processing apparatus according to the first embodiment shown in FIG. 2, the detailed description of the apparatus will be omitted herein.

Figure 9:
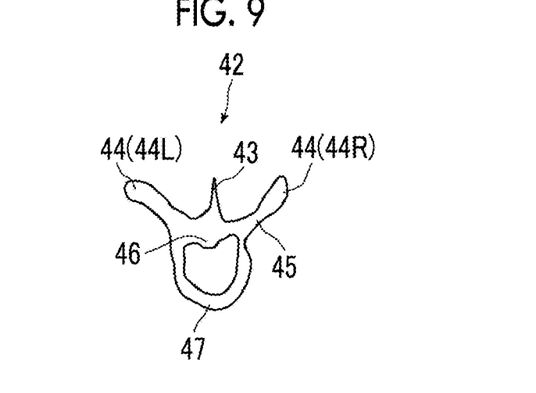
FIG. 9 is a diagram illustrating a plurality of anatomical regions in a cisternal region.

In the second embodiment, as shown in FIG. 9, the cisternal region extraction unit 22 divides the extracted cisternal region 42 into anatomical regions of a longitudinal cerebral fissure 43, a sylvian fissure 44, a sylvian valley 45, a basal cistern 46, and an ambient cistern 47. The division into anatomical regions may be performed by assigning a label of each anatomical region to each pixel in the cisternal region 32 of the standard brain image Bs and assigning the label assigned to each pixel in the cisternal region 32 to each corresponding pixel in the cisternal region 42 at the time of registration between the cisternal region 42 of the brain image B0 and the cisternal region 32 of the standard brain image Bs. In the second embodiment, attention is paid to the sylvian fissure 44, and the sylvian fissure 44 is divided into a left sylvian fissure 44L and a right sylvian fissure 44R.

In the second embodiment, the bleeding region specifying unit 23 specifies a bleeding region for each divided anatomical region. For example, as in the first embodiment described above, an index value indicating the difference in probability distribution between the first signal value distribution in the cisternal region 42 of the brain image B0 and the second signal value distribution in the cisternal region 32 of the standard brain image Bs is calculated for each divided anatomical region. Then, an anatomical region for which the calculated index value exceeds a predetermined threshold value Th2 is specified as a bleeding region. As a result, it is possible to check the presence or absence of bleeding for each anatomical region of the cisterna.

In this case, a probability value indicating the likelihood of being a cisternal region may be set for each pixel of the standard brain image Bs, and the first signal value distribution may be calculated for each anatomical region of the cisternal region 42 in the brain image B0 using the probability value.

In a case where the cisterna is divided into a plurality of anatomical regions as in the second embodiment, a bleeding region may be specified using a different parameter in each of the divided anatomical regions. For example, a case is considered in which, in a case where the index value calculated in each of the divided anatomical regions exceeds the threshold value Th2, the anatomical region is specified as a bleeding region. In this case, the threshold value Th2 is used as a parameter. Here, the standard brain image Bs used in the second embodiment is created using brain images of a plurality of healthy persons. In this case, the variance of the CT value is calculated for each anatomical region of the cisternal region included in a plurality of brain images. Then, the larger threshold value Th2 is set for an anatomical region having a larger variance of the CT value. In this manner, by specifying a bleeding region using a different parameter for each anatomical region, the conditions at the time of specifying a bleeding region become severer in an anatomical region having a large variation in CT value. As a result, it is possible to more accurately specify a bleeding region for each anatomical region of the cisterna.

Figure 10:
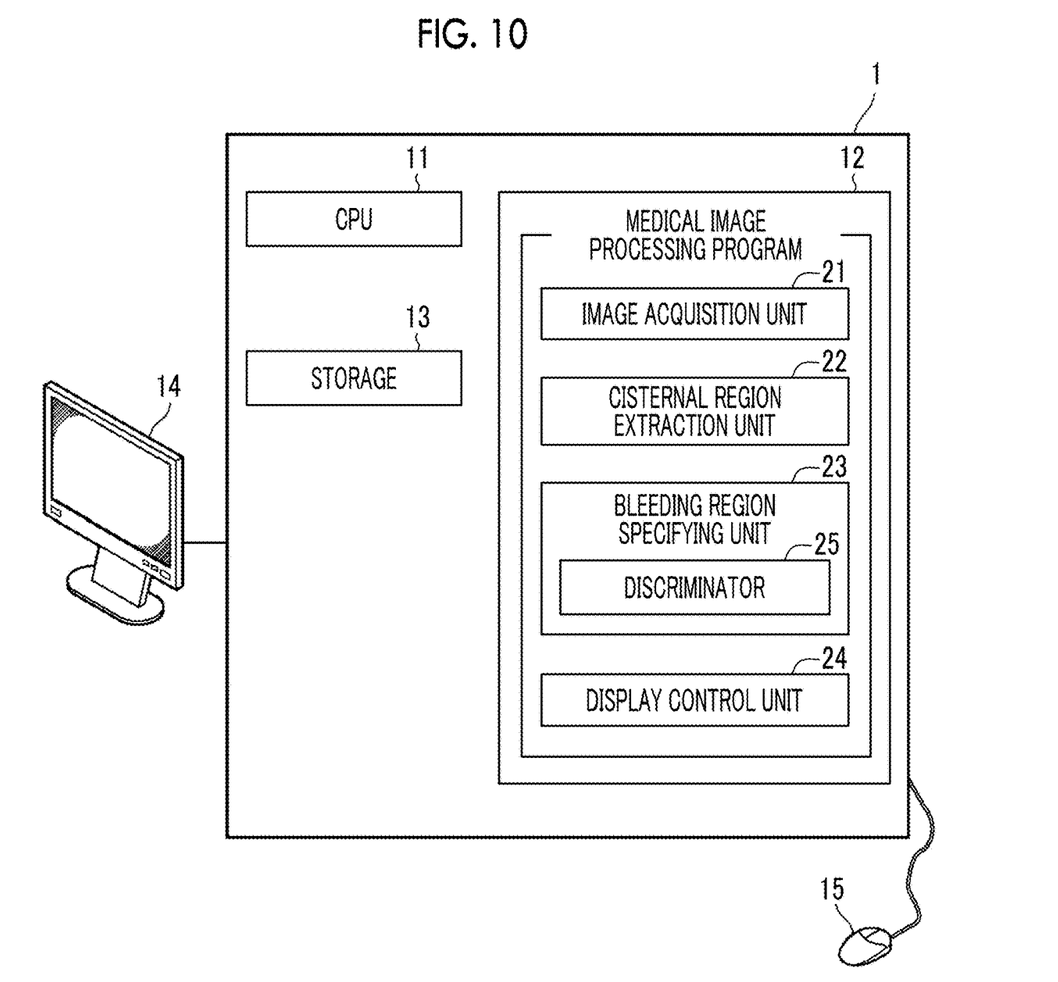
FIG. 10 is a diagram showing the schematic configuration of a medical image processing apparatus according to a third embodiment.

In the first embodiment described above, the bleeding region specifying unit 23 may comprise a discriminator to which a feature amount based on the first signal value distribution and the second signal value distribution is input and which outputs a bleeding region determination result. Hereinafter, this will be described as a third embodiment. FIG. 10 is a schematic block diagram showing the configuration of a medical image processing apparatus according to a third embodiment of the invention. In FIG. 10, the same components as in FIG. 2 are denoted by the same reference numerals, and the detailed description thereof will be omitted.

In the third embodiment, the bleeding region specifying unit 23 comprises a discriminator 25 to which a feature amount based on the first signal value distribution of the cisternal region 32 extracted from the brain image B0 and the second signal value distribution of the cisternal region 42 extracted from the standard brain image Bs is input and which outputs a bleeding region determination result. In the third embodiment, a difference between the first signal value distribution of the cisternal region 32 extracted from the brain image B0 and the second signal value distribution of the cisternal region 42 extracted from the standard brain image Bs is used as the feature amount.

In the third embodiment, for machine learning of the discriminator 25, a number of differences between the first signal value distribution and the second signal value distribution of a cisternal region, which is known to be a bleeding region, and a number of differences between the first signal value distribution and the second signal value distribution of a cisternal region, which is not a bleeding region, are prepared. Then, machine learning is performed using the number of differences, thereby generating the discriminator 25. As a method of machine learning, any known method using a logistic circuit, a support vector machine, and the like can be used. By performing learning in this manner, the discriminator 25 outputs a determination result as to whether or not the cisternal region 32 is a bleeding region in a case where the difference between the first signal value distribution of the cisternal region 32 extracted from the brain image B0 and the second signal value distribution of the cisternal region 42 extracted from the standard brain image Bs is input.

As in the third embodiment, it is also possible to specify a bleeding region by using the discriminator 25 to which the feature amount based on the first signal value distribution of the cisternal region 32 extracted from the brain image B0 and the second signal value distribution of the cisternal region 42 extracted from the standard brain image Bs is input and which outputs a determination result as to whether or not the cisternal region 32 is a bleeding region.

Also in the second embodiment described above, the bleeding region specifying unit 23 may comprise a discriminator. In the second embodiment, the discriminator may be created by performing machine learning so as to receive the difference between the first signal value distribution and the second signal value distribution for each of a plurality of anatomical regions as a feature amount and output a determination result as to whether or not the anatomical region is a bleeding region. As described above, also in the second embodiment, it is possible to specify a bleeding region using the discriminator.

In each of the embodiments described above, the CT image of the subject is used as a brain image. However, also in medical images other than CT images, such as MRI images and PET images, the pixel values are different between the normal cisternal region and the bleeding cisternal region. Therefore, a medical image other than the CT image may be used as a brain image.

Hereinafter, the effect of the present embodiment will be described.

In a case where a probability value indicating the likelihood of being a cisternal region is set for each pixel of the standard brain image, the first signal value distribution is calculated by weighting the pixel value of each pixel of the brain image registered with the standard brain image further based on the probability value. In this manner, a more appropriate signal value distribution for the cisternal region can be calculated as the first signal value distribution. Therefore, it is possible to more accurately specify a bleeding region.

The cisterna can be divided into anatomical regions, such as a longitudinal cerebral fissure, a sylvian fissure, a sylvian valley, a basal cistern, and an ambient cistern. Therefore, by dividing the cisternal region into a plurality of anatomical regions and specifying a bleeding region based on the first signal value distribution and the second signal value distribution for each of the plurality of anatomical regions, it is possible to check the presence or absence of bleeding in the anatomical region of the cisterna.

By specifying a bleeding region using a different parameter for each divided anatomical region, it is possible to more accurately specify a bleeding region for each anatomical region of the cisterna.

What is claimed is:
1. A medical image processing apparatus comprising:
an image acquisition circuit that acquires a brain image of a subject;
a cisternal region extraction unit that extracts a cisternal region from the brain image by performing registration between a standard brain image and the brain image; and
a bleeding region specifying circuit that specifies a bleeding region based on a first signal value distribution, which is a signal value distribution of the cisternal region extracted from the brain image, and a second signal value distribution, which is a signal value distribution of a cisternal region of the standard brain image, wherein the cisternal region extraction circuit further divides the cisternal region into a plurality of anatomical regions, and wherein the bleeding region specifying circuit specifies the bleeding region in each of the anatomical regions based on a first signal value distribution of each of the plurality of anatomical regions and a second signal value distribution of a region, which corresponds to each of the plurality of anatomical regions, in the standard brain image.

2. The medical image processing apparatus according to claim 1, wherein the bleeding region specifying circuit fits each of the first signal value distribution and the second signal value distribution to a predetermined probability density function, calculates a first probability distribution for the first signal value distribution and a second probability distribution for the second signal value distribution, calculates an index value indicating a difference between the first probability distribution and the second probability distribution, and specifies a cisternal region, which is extracted from the brain image for which the calculated index value exceeds a predetermined threshold value, as the bleeding region.

3. The medical image processing apparatus according to claim 1, wherein the bleeding region specifying circuit comprises a discriminator to which a feature amount based on the first signal value distribution and the second signal value distribution is input and which outputs a determination result as to whether or not the cisternal region is the bleeding region.

4. The medical image processing apparatus according to claim 1 wherein a probability value indicating a likelihood of being the cisternal region is set for each pixel of the standard brain image, and the bleeding region specifying circuit calculates the first signal value distribution by weighting a pixel value of each pixel of the brain image registered with the standard brain image further based on the probability value.

5. The medical image processing apparatus according to claim 1, wherein the cisternal region extraction unit further divides the cisternal region into a plurality of anatomical regions, and the bleeding region specifying circuit specifies the bleeding region based on a first signal value distribution of each of the plurality of anatomical regions and a second signal value distribution of a region, which corresponds to each of the plurality of anatomical regions, in the standard brain image.

6. The medical image processing apparatus according to claim 5, wherein the bleeding region specifying circuit specifies the bleeding region using a different parameter in each of the plurality of anatomical regions.

7. The medical image processing apparatus according to claim 5, wherein the bleeding region specifying circuit comprises a discriminator to which a feature amount based on the first signal value distribution and the second signal value distribution for each of the plurality of anatomical regions is input and which outputs a determination result as to whether or not the cisternal region is the bleeding region.

8. The medical image processing apparatus according to claim 1, wherein a probability value indicating a likelihood of being the cisternal region is set for each pixel of the standard brain image, and the bleeding region specifying circuit calculates the first signal value distribution for each of the plurality of anatomical regions by weighting a pixel value of each pixel of the brain image registered with the standard brain image further based on the probability value.

9. The medical image processing apparatus according to claim 1, wherein the brain image is a computed tomography (CT) image acquired by a CT apparatus.

10. The medical image processing apparatus according to claim 1, further comprising:

a display control unit that displays information indicating that the bleeding region has been specified on a display unit.

11. A medical image processing method comprising:

acquiring a brain image of a subject;

extracting a cisternal region from the brain image by performing registration between a standard brain image and the brain image; and specifying a bleeding region based on a first signal value distribution, which is a signal value distribution of the cisternal region extracted from the brain image, and a second signal value distribution, which is a signal value distribution of a cisternal region of the standard brain image, wherein the cisternal region is further divided into a plurality of anatomical regions, and wherein the bleeding region in each of the anatomical regions is specified based on a first signal value distribution of each of the plurality of anatomical regions and a second signal value distribution of a region, which corresponds to each of the plurality of anatomical regions, in the standard brain image.

12. A non-transitory computer-readable storage medium that stores a medical image processing program causing a computer to execute:

a step of acquiring a brain image of a subject;

a step of extracting a cisternal region from the brain image by performing registration between a standard brain image and the brain image; and a step of specifying a bleeding region based on a first signal value distribution, which is a signal value distribution of the cisternal region extracted from the brain image, and a second signal value distribution, which is a signal value distribution of a cisternal region of the standard brain image, wherein the cisternal region is further divided into a plurality of anatomical regions, and wherein the bleeding region in each of the anatomical regions is specified based on a first signal value distribution of each of the plurality of anatomical regions and a second signal value distribution of a region, which corresponds to each of the plurality of anatomical regions, in the standard brain image.

* * * * *